United States Patent
Tian et al.

(10) Patent No.: US 12,115,218 B2
(45) Date of Patent: Oct. 15, 2024

(54) IMMUNOLOGICAL ADJUVANT COMPOSITION, PREPARATION METHOD AND APPLICATION THEREOF

(71) Applicant: LUOYANG SEIWEI BIOTECHNOLOGIES CO., LTD., Hanan (CN)

(72) Inventors: Kegong Tian, Henan (CN); Yongmei Liu, Henan (CN); Xuke Zhang, Henan (CN)

(73) Assignee: LUOYANG SEIWEI BIOTECHNOLOGIES CO., LTD., Luoyang (CN)

( * ) Notice: Subject to any disclaimer, the term of this patent is extended or adjusted under 35 U.S.C. 154(b) by 695 days.

(21) Appl. No.: 17/312,441

(22) PCT Filed: Apr. 17, 2019

(86) PCT No.: PCT/CN2019/083106
§ 371 (c)(1),
(2) Date: Jun. 10, 2021

(87) PCT Pub. No.: WO2020/133817
PCT Pub. Date: Jul. 2, 2020

(65) Prior Publication Data
US 2022/0047699 A1 Feb. 17, 2022

(30) Foreign Application Priority Data
Dec. 24, 2018 (CN) .......................... 201811583863.0

(51) Int. Cl.
| A61K 39/39 | (2006.01) |
| A61K 39/02 | (2006.01) |
| A61K 39/12 | (2006.01) |
| A61K 39/187 | (2006.01) |
| A61K 39/245 | (2006.01) |
| A61P 31/04 | (2006.01) |
| A61P 31/20 | (2006.01) |
| A61K 39/00 | (2006.01) |

(52) U.S. Cl.
CPC .......... *A61K 39/39* (2013.01); *A61K 39/0241* (2013.01); *A61K 39/12* (2013.01); *A61K 39/187* (2013.01); *A61K 39/245* (2013.01); *A61P 31/04* (2018.01); *A61P 31/20* (2018.01); *A61K 2039/5252* (2013.01); *A61K 2039/55511* (2013.01); *A61K 2039/55577* (2013.01)

(58) Field of Classification Search
None
See application file for complete search history.

(56) References Cited

U.S. PATENT DOCUMENTS

2022/0047699 A1* 2/2022 Tian ....................... A61K 39/12

FOREIGN PATENT DOCUMENTS

| CN | 1367022 A | 9/2002 |
| CN | 1305524 C | 3/2007 |
| CN | 101240264 A | 8/2008 |
| CN | 103173470 A | 6/2013 |
| CN | 104450559 A | 3/2015 |
| CN | 104524563 A | 4/2015 |

OTHER PUBLICATIONS

Pulendran et al. (Nature Reviews Drug Discovery; 20(6) (2021): 454-475).*
Chopra et al. (Critical Reviews in Food Science and Nutrition. 2021; 63(5): 613-640).*
Mi et al. (Journal of Agricultural and Food Chemistry. 2023; 71 (24): 9391-9403).*
Pan et al. (Journal of Veterinary Diagnostic Investigation. 2008; 20: 448-456).*
Shin et al. (Journal of Ginseng Research; 2015; 39: 287-298).*
Xue et al. (Industrial Crops and Products. 2020; 143: 111929).*
Piao et al. (Molecules. 2020; 25: 3452).*

* cited by examiner

*Primary Examiner* — Shanon A. Foley
(74) *Attorney, Agent, or Firm* — John A. Miller; Shumaker, Loop & Kendrick, LLP

(57) ABSTRACT

The present disclosure provides an adjuvant composition containing 0.2%-15% w/v carbomer, 0.1%-0.5% w/v lecithin, and 0.03%-0.2% w/v ginsenoside. The adjuvant composition of the present disclosure cannot only ensure the long-term clarification and/or stability of the vaccine, but also can effectively stimulate the inactivated antigens and subunit antigens therein to produce high-titer antibodies for immune protection. The inactivated vaccines or subunit vaccines prepared by the adjuvant composition of the present disclosure can be used as a diluent for freeze-dried live virus antigens and has no toxic effect on the live virus antigens.

11 Claims, No Drawings

IMMUNOLOGICAL ADJUVANT COMPOSITION, PREPARATION METHOD AND APPLICATION THEREOF

CROSS-REFERENCE TO RELATED APPLICATIONS

This application is a National Stage application of International Application No. PCT/CN2019/083106 filed on Apr. 17, 2019, which claims priority to China Patent Application No. 201811583863.0 filed Dec. 24, 2018.

BACKGROUND

Field

The present disclosure belongs to the field of medical preparations, and relates to an immunological adjuvant composition, preparation method and application thereof.

Discussion of the Related Art

An "adjuvant" means a substance that enhances the humoral or cellular immune response to an antigen. Adjuvants are generally used to achieve two goals: controlled release of antigens from an injection site and stimulation of an immune system. Because adjuvants used in animals containing white oil for injection have strong side reactions, people have developed aqueous adjuvants, such as polyacrylic acid adjuvants represented by Carbopol™ (Carbomer) 934, including commercial GEL01 adjuvant of Seppic company. However, this type of aqueous adjuvants is only effective for some antigens, and it is less effective for other antigens. Moreover, if the polyacrylic acid solution is placed in an isotonic solution for a long time, the particles will become larger and form layers and precipitates, which will affect effect of the adjuvants.

A ginsenoside is also used as a veterinary adjuvant, for example, *Study on the effect of GSLS on improving the immune effect of foot-and-mouth disease and newcastle disease vaccines with oil adjuvants* (Yutao Li et al. 2012). However, the adjuvant effect of ginsenoside can only be manifested when it is used together with oil adjuvants.

In order to reduce stress in animals, inactivated vaccine is used as a diluent of live vaccine to achieve a "live+inactivated" means, which requires that the adjuvant of the inactivated vaccine itself has no virus-killing activity, while saponins such as commonly used Quil A are usually hemolytic, although saponins are added with cholesterol and lecithin to prepare immunostimulatory complex (ISCOM) with reduced virus-killing activity, it is found through the test that the complex still has a certain virus-killing activity and cannot be used as a diluent for live vaccines.

Immunity is complicated. When a common antigen is combined with different adjuvants, sometimes there is a synergistic effect and sometimes an antagonistic effect. Different antigens have different selected adjuvants due to their different immune mechanisms. Therefore, there is a need in the art for an immune adjuvant, which is stable during the validity period, easy to prepare, has a significant enhancement effect on commonly used antigens, and can form a vaccine composition with an inactivated vaccine to dilute a live vaccine. Although there are many adjuvants disclosed in the prior art, how to solve these three problems at the same time is still a problem for those skilled in the art.

SUMMARY

To solve the above technical problems, the present disclosure provides an adjuvant composition, wherein the adjuvant composition contains 0.2%-15% w/v carbomer, 0.1%-0.5% w/v Lecithin, and 0.03%-0.2% w/v ginsenoside.

The inventor suprisingly discovered that when ginsenoside is added to the solution of carbomer and lecithin, the adjuvant becomes clear, the stability of the adjuvant is improved, and at this concentration, ginsenoside alone has no immune enhancing effect but can act as a stabilizer. The added ginsenoside has a stabilizing effect in a certain concentration range (0.03%-0.2% w/v). This range has little to do with the concentration of carbomer and lecithin, and it is found that it is not a known component of any immune-enhancing chemical composition.

The adjuvant composition of the present disclosure can be combined with an antigen in a volume ratio of (30-70):50, which can not only ensure that the vaccine is clear and stable for up to 12 months at 4° C., stable for up to 6 months at 25° C., and stable for 3 months at 37° C.; but also effectively stimulate the inactivated antigen and subunit antigen to produce high-titer antibodies for immune protection.

In the adjuvant composition of the present disclosure, content of the carbomer can be selected from 0.2% w/v, 0.25% w/v, 0.3% w/v, 0.35% w/v, 0.4% w/v, 0.45% w/v and 0.5% w/v; content of the lecithin can be selected from 0.1% w/v, 0.15% w/v, 0.2% w/v, 0.25% w/v, 0.3% w/v, 0.35% w/v, 0.4% w/v, 0.45% w/v, and 0.5% w/v, content of the ginsenoside can be selected from 0.03% w/v, 0.04% w/v, 0.05% w/v, 0.06% w/v, 0.07% w/v, 0.08% w/v, 0.09% w/v, 0.1% w/v, 0.11% w/v, 0.12% w/v, 0.13% w/v, 0.14% w/v, 0.15% w/v, 0.16% w/v, 0.17% w/v, 0.18% w/v, 0.19% w/v, and 0.2% w/v.

As an embodiment of the present disclosure, in the adjuvant composition of the present disclosure, the adjuvant composition contains 0.2%-0.5% w/v carbomer, 0.1%-0.4% w/v lecithin and 0.03%-0.2% w/v ginsenoside.

As a preferred embodiment of the present disclosure, in the adjuvant composition of the present disclosure, the adjuvant composition contains 0.2%-0.5% w/v carbomer, 0.1%-0.2% w/v lecithin and 0.03%-0.2% w/v ginsenoside.

As a more preferred embodiment of the present disclosure, in the adjuvant composition of the present disclosure, the adjuvant composition contains 0.4% w/v carbomer, 0.1% w/v lecithin and 0.05% w/v ginsenoside.

As an embodiment of the present disclosure, in the adjuvant composition of the present disclosure, the adjuvant composition further contains 0.05%-0.2% w/v polyinosinic acid-polycytidylic acid or derivatives thereof.

In the adjuvant composition of the present disclosure, content of the polyinosinic acid-polycytidylic acid or derivatives thereof of the present disclosure may be selected from 0.05% w/v, 0.06% w/v, 0.07% w/v, 0.08% w/v, 0.09% w/v, 0.10% w/v, 0.11% w/v, 0.12% w/v, 0.13% w/v, 0.14% w/v, 0.15% w/v v, 0.16% w/v, 0.17% w/v, 0.19% w/v and 0.2% w/v.

The adjuvant composition of the present disclosure, after adding polyinosinic acid-polycytidylic acid or derivatives thereof, can further stimulate the inactivated antigen and subunit antigen therein to produce high-titer antibodies, and the immune effect is remarkable.

The present disclosure also provides a first vaccine composition, wherein the first vaccine composition contains 30-70% w/w the adjuvant composition and an immune amount of inactivated antigen or subunit antigen.

As an embodiment of the present disclosure, in the first vaccine composition of the present disclosure, content of the adjuvant composition is 50% w/w.

In the adjuvant composition of the present disclosure, the content of the adjuvant composition may be selected from 30% w/w, 35% w/w, 40% w/w, 45% w/w, 50% w/w, 55% w/w, 60% w/w, 65% w/w, and 70% w/w.

The first vaccine composition of the present disclosure can be protected by a single-shot immunization.

As an embodiment of the present disclosure, in the first vaccine composition of the present disclosure, the inactivated antigen is porcine circovirus antigen, *Mycoplasma hyopneumoniae* antigen or porcine pseudorabies virus antigen.

The adjuvant composition of the present disclosure can be used in combination with various inactivated antigens or subunit antigens, which can effectively enhance the immune effect of these antigens. These antigens can be porcine circovirus antigen, *Mycoplasma hyopneumoniae* antigen, porcine pseudorabies virus antigen, *Haemophilus parasuis* antigen, porcine reproductive and respiratory syndrome virus antigen, porcine parvovirus antigen, *Pasteurella multocida* antigen, *Streptococcus suis* antigen, *Staphylococcus* suis antigen, *Bordetella* bronchitis antigen, *Salmonella choleraesuis* antigen, *Salmonella enteritidis* antigen, porcine respiratory coronavirus antigen, porcine epidemic diarrhea virus antigen, porcine rotavirus antigen, porcine transmissible gastroenteritis virus antigen, porcine torque teno virus antigen, porcine cytomegalovirus antigen, encephalomyocarditis virus antigen, swine influenza virus antigen, swine fever virus antigen or a combination thereof.

As a preferred embodiment of the present disclosure, in the first vaccine composition of the present disclosure, the inactivated antigen is an inactivated whole virus antigen of porcine circovirus type 2 SH strain, of which the accession number is CGMCC No. 2389.

The porcine circovirus type 2 SH strain was deposited at the China General Microbiological Culture Collection Center (CGMCC) on Mar. 4, 2008, with the accession number of CGMCC No. 2389, which was published in CN101240264A. The address of CGMCC is No. 3, Yard 1, Beichen West Road, Chaoyang District, Beijing City, China.

The inactivated whole virus antigen of the porcine circovirus type 2 SH strain in the first vaccine composition of the present disclosure can produce immune protection after one single-shot immunization.

As an embodiment of the present disclosure, in the first vaccine composition of the present disclosure, the first vaccine composition contains 0.2% w/v carbomer, 0.05% w/v lecithin, 0.015%-0.05% w/v ginsenoside and 100 μg/ml PCV2 protein virus-like particle antigen.

The PCV2 protein virus-like particle antigen in the first vaccine composition of the present disclosure can generate immune protection after one single-shot immunization, and the duration of immunity can be as long as 20 weeks.

As a preferred embodiment of the present disclosure, in the first vaccine composition of the present disclosure, the first vaccine composition contains 0.2% w/v carbomer, 0.05% w/v lecithin, 0.025% w/v ginsenoside, 0.025%-0.1% w/v polyinosinic acid-polycytidylic acid or derivatives thereof, and 100 μg/ml PCV2 protein virus-like particle antigen.

As an embodiment of the present disclosure, in the first vaccine composition of the present disclosure, the first vaccine composition contains 0.2% w/v carbomer, 0.05% w/v lecithin, 0.025% w/v ginsenoside, 0.025%-0.1% w/v polyinosinic acid-polycytidylic acid or derivatives thereof and inactivated whole-bacteria antigen of HN0613 strain of which content of bacteria before inactivation is $1.5 \times 10^9$ CCU/ml and the accession number is CCTCC M2012230, where HN0613 strain is a *Mycoplasma hyopneumoniae* strain, which is deposited in China Center for Type Culture Collection (CCTCC) on Jun. 13, 2012, of which the address is Wuhan University, Wuhan, China.

The inactivated whole-bacteria antigen of HN0613 strain in the first vaccine composition of the present disclosure can produce immune protection without side effects after one single-shot immunization. The inactivated vaccine prepared by the disclosure does not cause inflammation, turning red and swelling at the injection site of pigs after injection, and has better stability, and can be combined with vaccines to obtain better immune efficacy and used in large-scale production.

In certain embodiments of the present disclosure, the first vaccine composition may include one or more other components, such as surfactants, buffers, and stabilizing compounds.

As a preferred embodiment of the present disclosure, in the first vaccine composition of the present disclosure, the vaccine composition further includes a surfactant, a buffer, and a stabilizing compound.

The present disclosure also provides a second vaccine composition, wherein the second vaccine composition comprises the first vaccine composition and an immune amount of live virus vaccine.

The adjuvant composition of the present disclosure has no virus-killing activity and can be used for dilution of live vaccines against swine fever virus and swine pseudorabies virus. The vaccine complex formed from combination of the adjuvant composition of the present disclosure and inactivated antigens or subunit antigens can be used to dilute live vaccines. By comparing with the reference diluent, the effect of the adjuvant composition of the present disclosure on the viral activity is evaluated, and the difference is not more than 0.7 log 10 (European Veterinary Vaccine Standard).

As an embodiment of the present disclosure, in the second vaccine composition of the present disclosure, the live virus vaccine is a swine reproductive and respiratory syndrome live vaccine, a swine fever live vaccine or a pseudorabies live vaccine.

As a preferred embodiment of the present disclosure, in the second vaccine composition of the present disclosure, the swine reproductive and respiratory syndrome live vaccine is JXA1-R strain, the swine fever live vaccine is attenuated strain of Hog cholera lapinized virus (HCLV), and the pseudorabies live vaccine are Bartha-K61 strain.

The present disclosure also provides a preparation method of the adjuvant composition, wherein the preparation method includes:

a) dissolving acrylic polymer in water to prepare an aqueous solution of acrylic polymer;

b) dissolving lecithin in ethanol to prepare an ethanol solution of lecithin;

c) dissolving Ginsenoside in water to prepare an aqueous solution of ginsenoside; and d) combining the aqueous solution of acrylic polymer, the ethanol solution of lecithin and the aqueous solution of ginsenoside together.

The adjuvant of the present disclosure does not contain mineral oil and metabolizable oil. No emulsification equipment is needed for the preparation, and the preparation process is simple.

DETAILED DESCRIPTION OF THE EMBODIMENTS

The term "adjuvant" refers to a compound that enhances the subject's immune response to an antigen when administered together with the antigen. Adjuvant-mediated enhancement of immune response can be assessed by any methods known in the art, including (but not limited to) one or more of the following methods: (i) compared with the number of antibodies produced in response to the immune effect of the antigen alone, the number of antibodies produced in response to the immune effect of the adjuvant/antigen combination increases; (ii) the number of T cells that recognize the antigen or adjuvant increases; (iii) the content of one or more type I cytokines increases; and (iv) the protective effect in vivo after being challenged. Any measurable parameter of antigen-specific immunoreactivity (eg, production of antibody titer or T cell) is increased by at least 10% when the subject is challenged with antigens and adjuvant compared to subjects challenged with antigens alone, it is considered that the immune response is enhanced. In certain embodiments of the disclosure, if any measurable parameter of antigen-specific immunoreactivity is increased by at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 350%, at least 400%, at least 450%, at least 500%, or at least 1000%, the immune response is enhanced.

An "acrylic polymer" means any polymer or copolymer containing an acrylic portion. Exemplary acrylic polymers include, for example, polyacrylic acid, methacrylic acid, methacrylates, acrylamide, acrylates, acrylonitrile, and alkyl esters of polyacrylic acid. Examples of acrylic copolymers include, for example, poly(acrylamide-co-butyl methacrylate), acrylic acid-methacrylic acid polymers, acrylic acid-acrylamide polymers, and polymethacrylates. Examples of commercially available acrylic polymers include carbomer, which in the art generally also refers to and is known as a water-soluble polymer of acrylic acid cross-linked with polyallyl sucrose. The amount used is usually about 0.0001% by volume (v/v) to about 75% v/v. In other embodiments, the amount used is selected from about 0.001% v/v to about 50% v/v, about 0.005% v/v to about 25% v/v, about 0.01% v/v to about 10% v/v, about 0.05% v/v to about 2% v/v, and about 0.1% v/v to about 0.75% v/v. In another embodiment, the amount used is from about 0.02% v/v to about 0.4% v/v.

The term "lecithin" is also called phosphatidylcholine, such as lecithin from soybean or egg yolk. By washing the crude vegetable oil with water, and then separating and drying the resulting hydrated gum, lecithin can be obtained as a mixture of phospholipids and triglycerides. After removing triglycerides and vegetable oil in acetone, the remaining acetone-insoluble mixture of phospholipids and glycerides can be fractionated to obtain a refined product. Alternatively, lecithin can be obtained from different commercial sources. The amount of lecithin used is generally selected from about 0.001% v/v to about 50% v/v, about 0.005% v/v to about 25% v/v, about 0.01% v/v to about 10% v/v, about 0.05% v/v to about 2% v/v and about 0.1% v/v to about 0.75% v/v. In another embodiment, the amount used is from about 0.02% v/v to about 0.4% v/v.

The term "ginsenoside" is a steroid compound, triterpene saponin, which mainly exists in ginseng herbs, including ginseng stem-leaf saponins and ginseng root saponins. The quality standards of commercial total ginseng stem-leaf saponins and total ginseng saponins are included in the Pharmacopoeia of the People's Republic of China. The amount of ginsenoside used is usually selected from about 0.03% v/v to about 0.2% v/v, about 0.01% v/v to about 0.05% v/v, about 0.05% v/v to about 0.1% v/v, and about 0.03% v/v to about 0.2% v/v.

As described herein, "polyinosinic acid-polycytidylic acid or derivatives thereof" include but are not limited to polyinosinic acid-polycytidylic acid, "PICKCa", poly I:C (CAS 24424-50-0, Oligochitosan-Kanamycin-Poly(I:C) sodium salt), where the term PICKCa generally refers to the complex composed of poly I:C, kanamycin and calcium chloride. The terms "poly I:C" or "PIC" refer to compositions containing polyriboinosinic polyribocytidylic acid, also known as polyinosinic acid-polycytidylic acid, respectively. The amount used is usually about 1 µg to about 5000 µg per dose. The amount used can also be selected from about 1 µg to about 4000 µg per dose, about 1 µg to about 3000 µg per dose, about 1 µg to about 2000 µg per dose, and about 1 µg to about 1000 µg per dose. The amount used can also be selected from about 5 µg to about 750 µg per dose, about 5 µg to about 500 µg per dose, about 5 µg to about 200 µg per dose, about 5 µg to about 100 µg per dose, about 15 µg to about 100 µg and about 30 µg to about 75 µg per dose.

The term "vaccine composition" is a composition that can be used to induce protective immunity in a subject. Therefore, after a subject has been vaccinated with an antigen, the vaccine can prevent, delay, or reduce the severity of disease development in the subject exposed to the same or related antigen (relative to an unvaccinated subject). The protective immunity provided by the vaccine may be humoral (antibody-mediated) immunity or cellular immunity, or both.

The term "antigen" refers to an agent that is recognized by a host's immune system when it is introduced into a subject and is capable of inducing an immune response and generating protective immunity. Antigens include, but are not limited to, "surface antigens" naturally expressed on the surface of pathogens or infected cells or tumor cells. Non-limiting examples of antigens which can induce protective immunity against disease pathogens and/or pathologies, are porcine circovirus antigen, *Mycoplasma hyopneumoniae* antigen, porcine pseudorabies virus antigen, *Haemophilus parasuis* antigen, porcine reproductive and respiratory syndrome virus antigen, porcine parvovirus antigen, *Pasteurella multocida* antigen, *Streptococcus suis* antigen, *Staphylococcus* suis antigen, *Bordetella* bronchitis antigen, *Salmonella choleraesuis* antigen, *Salmonella enteritidis* antigen, porcine respiratory coronavirus antigen, porcine epidemic diarrhea virus antigen, porcine rotavirus antigen, porcine transmissible gastroenteritis virus antigen, porcine torque teno virus antigen, porcine cytomegalovirus antigen, encephalomyocarditis virus antigen, swine influenza virus antigen, swine fever virus antigen or a combination thereof.

In some embodiments, the antigen is a porcine circovirus antigen.

In certain embodiments, the antigen is a *Mycoplasma hyopneumoniae* antigen.

In some embodiments, the antigen is a porcine pseudorabies virus antigen.

The description of the present disclosure is further provided as follows with reference to the specific embodiments, and features and advantages of the present disclosure will become more apparent from the following description. However, these embodiments are merely exemplary and do not limit the scope of the present disclosure in any way. It should be understood by a person skilled in the art that modifications or alternatives to details and forms of the technical solution of the present disclosure without deviation from the spirit and scope of the present disclosure will be allowed, while those modifications and alternatives should all fall within the scope of the present disclosure.

The chemical reagents used in the examples of the present disclosure are of analytical grade and are purchased from Sinopharm Group Co. Ltd.

In order to make the present disclosure more understandable, the present disclosure will be further described with reference to specific embodiments. The experimental methods described in the present disclosure are conventional methods unless otherwise specified. The biological materials are commercially available unless otherwise specified.

Example 1 Preparation of Carbomer Solution 1 g of Carbomer 934 was added to 50 ml of water, stirred to dissolve, and then added with 1.5 g of sodium chloride solution. The pH of the solution was adjusted to 7.0 with sodium hydroxide solution. After autoclaving, the solution was ready for use, with a content of 2% w/v.

Example 2 Preparation of Ethanol Solution of Lecithin 5 g of lecithin (PC90, manufactured by Jiangsu Maxim Biological Co., Ltd.) was added to 100 ml of ethanol, and stirred to dissolve. After being filtered with a 0.22 μm filter membrane, the solution was ready for use, with a content of 5% w/v.

Example 3 Preparation of Ginsenoside Solution 1 g of ginseng stem-leaf saponins (containing 67.7% total saponins, produced by Jilin Hongjiu Biotechnology Co., Ltd.) were added to 100 ml of water, and stirred to dissolve. After being filtered with a 0.22 μm filter membrane, the solution was ready for use, with a content of 1% w/v.

Example 4 Polyinosinic Acid-Polycytidylic Acid Aqueous Solution 1 g of polyinosinic acid-polycytidylic acid (Hangzhou Meiya Pharmaceutical Co., Ltd.) was added to 100 ml of water, and stirred to dissolve. After being filtered with a 0.22 μm filter membrane, the solution was ready for use, with a content of 1% w/v.

Example 5 Levamisole Aqueous Solution 1.8 g of levamisole hydrochloride was added to 80 ml of water, stirred to dissolve, of which the pH was adjusted to 7.0 with 0.5M sodium hydroxide solution, and diluted to 100 ml with water for injection. After being filtered with a 0.22 μm filter membrane, the solution was ready for use, with a content of 1.8% w/v.

Example 6 Quil A Solution 0.6 g of Quil A was added to 100 ml of water and stirred to dissolve. After being filtered with a 0.22 μm filter membrane, the solution was ready for use, with a content of 0.6% w/v.

Example 7 Preparation of Adjuvants and Preparation of Vaccines with Adjuvants for Stability Test Adjuvant compositions were prepared by adding the carbomer solution, ethanol solution of lecithin, ginsenoside solution, polyinosinic acid-polycytidylic acid (or called polyinosinic-polycytidylic acid) aqueous solution, levamisole aqueous solution or Quil A solution according to the amounts in Table 1, of which the volume was adjusted up to 100 ml with a pH 7 PBS solution. There was no strict restriction on the order of adding the carbomer solution, ethanol solution of lecithin, ginsenoside solution and polyinosinic acid-polycytidylic acid aqueous solution was not strictly limited.

TABLE 1

Preparation of adjuvant compositions and the contrast adjuvant compositions

| No. | Carbomer solution | ethanol solution of Lecithin | Ginsenoside solution | Polyinosinic acid-polycytidylic acid aqueous solution | Levamisole aqueous solution | Quil A solution |
|---|---|---|---|---|---|---|
| Test example 1 | 20 ml | 2 ml | 1 ml | — | — | — |
| Test example 2 | 20 ml | 2 ml | 3 ml | — | — | — |
| Test example 3 | 20 ml | 2 ml | 10 ml | — | — | — |
| Test example 4 | 20 ml | 2 ml | 20 ml | — | — | — |
| Test example 5 | 20 ml | 2 ml | 30 ml | — | — | — |
| Test example 6 | 20 ml | 2 ml | 5 ml | 5 ml | — | — |
| Test example 7 | 20 ml | 2 ml | 5 ml | 20 ml | — | — |
| Test example 8 | 10 ml | 2 ml | 5 ml | — | — | — |

TABLE 1-continued

Preparation of adjuvant compositions and the contrast adjuvant compositions

| No. | Carbomer solution | ethanol solution of Lecithin | Ginsenoside solution | Polyinosinic acid-polycytidylic acid aqueous solution | Levamisole aqueous solution | Quil A solution |
|---|---|---|---|---|---|---|
| Test example 9 | 15 ml | 2 ml | 5 ml | — | — | — |
| Test example 10 | 25 ml | 2 ml | 5 ml | — | — | — |
| Test example 11 | 20 ml | 4 ml | 5 ml | — | — | — |
| Test example 12 | 20 ml | 4 ml | 5 ml | 5 ml | — | — |
| Test example 13 | 20 ml | 8 ml | 5 ml | 5 ml | — | — |
| Test example 14 | 20 ml | 10 ml | 5 ml | 5 ml | — | — |
| Contrast example 1 | 20 ml | — | — | — | — | — |
| Contrast example 2 | 20 ml | 2 ml | — | — | — | — |
| Contrast example 3 | 20 ml | — | 3 ml | — | — | — |
| Contrast example 4 | 20 ml | — | — | — | 10 ml | — |
| Contrast example 5 | 20 ml | 2 ml | — | — | — | 10 ml |

Influence on a Stability Test

Vaccines were prepared of which a stability test was conducted. The antigen of inactivated porcine circovirus type 2 vaccine (SH strain) were added with the adjuvants of Table 1, at a ratio of 1:1 (volume ratio of antigen and adjuvant), mixed and stirred evenly, placed at 4° C., 25° C., 37° C., to observe the stability of their traits. Observation was conducted day by day within 7 days; once a week after 7 days to one month; then once a month. Observation was conducted at 4° C. for 1 year, at 25° C. for 6 months, and at 37° C. for 3 months. The time when the stability was unqualified was recorded, see Table 2. The porcine circovirus type 2 SH strain has an accession number of CGMCC No. 2389 and the porcine circovirus type 2 SH strain was deposited at the the China General Microbiological Culture Collection Center on Mar. 4, 2008, with the accession number of CGMCC No. 2389, which was published in CN101240264A.

TABLE 2

Results of the stability test

| No. | Stability at 4° C. | Stability at 25° C. | Stability at 37° C. |
|---|---|---|---|
| Test example 1 | The vaccine was not clear, and precipitation occured within 8 months | Precipitation occurred within 3 months | Stable within 3 months |
| Test example 2 | The vaccine was clear, and stable within 12 months | Stable within 6 months | Stable within 3 months |
| Test example 3 | The vaccine was clear, and stable within 12 months | Stable within 6 months | Stable within 3 months |
| Test example 4 | The vaccine was clear, and stable within 12 months | Stable within 6 months | Stable within 3 months |
| Test example 5 | The vaccine was clear, and precipitation occured within 1 month | precipitation occured within 7 days | precipitation occured |
| Test example 6 | The vaccine was clear, and stable within 12 months | Stable within 6 months | Stable within 3 months |
| Test example 7 | The vaccine was clear, and stable within 12 months | Stable within 6 months | Stable within 3 months |
| Test example 8 | The vaccine was clear, and stable within 12 months | Stable within 6 months | Stable within 3 months |
| Test example 9 | The vaccine was clear, and stable within 12 months | Stable within 6 months | Stable within 3 months |
| Test example 10 | The vaccine was clear, and stable within 12 months | Stable within 6 months | Stable within 3 months |
| Test example 11 | The vaccine was clear, and stable within 12 months | Stable within 6 months | Stable within 3 months |

TABLE 2-continued

Results of the stability test

| No. | Stability at 4° C. | Stability at 25° C. | Stability at 37° C. |
|---|---|---|---|
| Test example 12 | The vaccine was in suspension and stable within 12 months. | Stable within 6 months | Stable within 3 months |
| Test example 13 | The vaccine was in suspension and stable within 12 months. | Stable within 6 months | Stable within 3 months |
| Test example 14 | The vaccine was in suspension, and precipitation occured within 8 months | Precipitation occurred within 3 months | Precipitation occurred within 10 days |
| Contrast example 1 | The vaccine was clear, and obvious stratification occured within 7 days | Obvious stratification occurred after 3 day | Obvious stratification occurred after 1 day |
| Contrast example 2 | Vaccine was turbid, and obvious stratification occured within 7 days | Obvious stratification occurred after 3 day | Obvious stratification occurred after 1 day |
| Contrast example 3 | Vaccine was clear, and obvious precipitation occured within 7 days | Obvious precipitation occurred within 3 days | Obvious precipitation occurred after 1 day |
| Contrast example 4 | Vaccine was turbid, and obvious precipitation occurred within 7 days | Obvious precipitation occurred within 7 days | Obvious precipitation occurred after 1 day |
| Contrast example 5 | Vaccine was turbid, and obvious stratification occurred within 7 days | Obvious stratification occurred after 3 day | Obvious stratification occurred after 1 day |

The results of the stability test showed that when the adjuvant was prepared by carbomer alone, the vaccine would be stratified obviously at 4° C. in the stability test; when the adjuvant was prepared with carbomer and lecithin, the vaccine was not clear, and there was obvious stratification in the stability test; when the adjuvant was composed of carbomer and levamisole or composed of carbomer and Quil A, precipitation would still occurred. However, when the vaccine was prepared with an adjuvant which is prepared by combining carbomer, ethanol solution of lecithin and ginsenoside, the vaccine became clear. The amount of ginsenoside added needs to be within a certain range. When the added amount is too small (1 ml), the vaccine prepared with the adjuvant was still not clear; and when adding a large amount (30 ml), the vaccine prepared with the adjuvant was prone to precipitation.

Example 8. Immune Enhancement Effects of Adjuvants on Porcine Circovirus Vaccine in Mice The mouse immunization was conducted under quality standard of Porcine Circovirus Type 2 Vaccine, Inactivated (Strain SH, II), which belongs to Porcine Circovirus Vaccine in Announcement No. 2442 by the Ministry of Agriculture and the same antigen was determined. Inactivated porcine circovirus type 2 vaccine (SH strain) antigen was used with adjuvants of Table 1 and adjuvants of contrast examples 6-14 in Table 3. The ratio of antigen to adjuvant was 1:1 (volume ratio). The mixtures were stirred well after mixing and then tested.

TABLE 3

Immune enhancement test of adjuvants on porcine circovirus vaccine in mice

| No. | Fomulations of adjuvants | Antibody titers in mice |
|---|---|---|
| Adjuvant of test example 2 | Test example 2 in the formulation of Table 1 | 1:1600 |
| Adjuvant of test example 3 | Test example 3 in the formulation of Table 1 | 1:1700 |
| Adjuvant of test example 4 | Test example 4 in the formulation of Table 1 | 1:1800 |
| Adjuvant of test example 6 | Test example 6 in the formulation of Table 1 | 1:11000 |
| Adjuvant of test example 7 | Test example 7 in the formulation of Table 1 | 1:12000 |
| Adjuvant of test example 8 | Test example 8 in the formulation of Table 1 | 1:1700 |
| Adjuvant of test example 9 | Test example 9 in the formulation of Table 1 | 1:1500 |
| Adjuvant of test example 10 | Test example 10 in the formulation of Table 1 | 1:1800 |
| Adjuvant of test example 11 | Test example 11 in the formulation of Table 1 | 1:1900 |
| Adjuvant of test example 12 | Test example 12 in the formulation of Table 1 | 1:1900 |
| Adjuvant of test example 13 | Test example 13 in the formulation of Table 1 | 1:1800 |
| Adjuvant of test example 14 | Test example 14 in the formulation of Table 1 | 1:1800 |
| Adjuvant of contrast example 1 | Contrast example 1 in the formulation of Table 1 | 1:800 |
| Adjuvant of contrast example 2 | Contrast example 2 in the formulation of Table 1 | 1:900 |
| Adjuvant of contrast example 3 | Contrast example 3 in the formulation of Table 1 | 1:800 |
| contrast example 6 | 0.18% Levamisole aqueous solution | Less than 1:200 |
| contrast example 7 | 5 ml of ginsenoside solution prepared in Example 3, of which the volume was adjusted up to 100 ml with a PBS solution of pH 7 | Less than 1:200 |
| contrast example 8 | 10 ml of ginsenoside solution prepared in Example 3, of which the volume was adjusted up to 100 ml with a PBS solution of pH 7 | Less than 1:200 |
| contrast example 9 | 20 ml of ginsenoside solution prepared in Example 3, of which the volume was adjusted up to 100 ml with a PBS solution of pH 7 | Less than 1:200 |
| contrast example 10 | 20 g of aluminum gels and 20 ml of ginsenoside solution prepared in Example 3, of which the volume was adjusted up to 100 ml with a PBS solution of pH 7 | Less than 1:800 |
| contrast example 11 | 0.06% Quil A aqueous solution | Less than 1:200 |
| contrast example 12 | 0.1% polyinosinic acid-polycytidylic acid aqueous solution | Less than 1:200 |
| contrast example 13 | 0.18% levamisole aqueous solution | Less than 1:200 |
| contrast example 14 | 2 ml of ethanol solution of lecithin, of which the volume was adjusted up to 100 ml with a PBS solution of pH 7 | Less than 1:200 |

The test results show that when the ginsenoside, Quil A, polyinosinic acid-polycytidylic acid, levamisole aqueous solution or lecithin solution was used alone, no adjuvant synergistic effect was produced, the antibody titers in mice were not significant enhanced, and the antibody titers for ginsenoside+aluminum gel were only at most 1:800, the antibody titers in mice for ginsenoside and carbomer is not much different from that of carbomer alone, but the combination of ginsenoside+carbomer+lecithin can significantly increase the antibody titers in mice. The combination of ginsenoside+carbomer+lecithin+polyinosinic acid-polycytidylic acid has greatly improved the antibody titers in mice.

Example 9 Preventive Effects of the Vaccine Compositions Prepared by the Adjuvants of the Present Disclosure on Porcine Circovirus Vaccines were prepared according to Table 4. For porcine circovirus antigens, according to CN103173470A, PCV2 protein virus-like particle antigen was prepared. The final product vaccine contains 100 μg of PCV2 protein in 1 ml. Adjuvants were added according to Table 4, to prepare vaccines of which the volume was adjusted up to 100 ml with a PBS solution of pH 7.0. The vaccines were ready to use after being stirred well. 21-day-old antibody-negative piglets were selected. 10 pigs per group were injected with the vaccines of Table 4, and blood samples were collected after 4 weeks and 20 weeks after immunization. The serum was separated and tested for antibodies with the biochek ELISA test kit. The test results are shown in Table 4.

TABLE 4

Porcine circovirus antibody detection in piglets injected with the vaccine compositions prepared by the adjuvants of the present disclosure

| Group | Adjuvants for vaccine | biochek(S/P) four weeks after immunization | biochek(S/P) 20 weeks after immunization |
|---|---|---|---|
| Vaccine A | Added 50% (v/v) adjuvant prepared according to Test example 2 of Example 3 | 1.41 | 0.53 |
| Vaccine B | Added 50% (v/v) adjuvant prepared according to Test example 3 of Example 3 | 1.59 | 0.69 |
| Vaccine C | Added 50% (v/v) adjuvant prepared according to Test example 6 of Example 3 | 1.71 | 1.51 |
| Vaccine D | Added 50% (v/v) adjuvant prepared according to Test example 7 of Example 3 | 1.75 | 1.38 |
| Contrast vaccine A1 | Added 10% (v/v) GEL01 (Seppic) | 0.85 | 0.49 |
| Contrast vaccine B1 | Added 50% (v/v) adjuvant prepared according to Contrast example 4 of Example 3 | 0.89 | 0.18 |
| Contrast vaccine C1 | Added 50% (v/v) adjuvant prepared according to Contrast example 2 of Example 3 | 0.76 | 0.35 |

Evaluation criteria: positive, where S/P value≥0.5 (titer 1071); negative, where S/P value≤0.499 (titer 1070).

As can be seen from the test results, compared with the cases of adjuvants of three groups of vaccines A1-C1, where antibodies can not be maintained for 4 months after one single-shot immunization, the vaccines prepared with adjuvant compositions of Test examples 2-3, 6-7 of the present disclosure can be maintained for 20 weeks, and the antibodies were still positive after 20 weeks, while the antibody titers of the vaccine groups C and D were significantly higher.

Example 10 Preventive Effects of the Vaccine Compositions Prepared by the Adjuvants of the Present Disclosure on Mycoplasma hyopneumoniae

*M. hyopneumoniae* HN0613 strain was selected as the antigen (HN0613 strain, accession number CCTCC M2012230, disclosed in CN104450559A), and the antigen solution was prepared according to the method of Example 2 of the patent CN104450559A, and the final product vaccine of 2 ml contained a content of $3 \times 10^9$ CCU of the bacteria before inactivation. Adjuvants were added according to Table 5, to prepare vaccines of which the volume was adjusted up to 100 ml with a PBS solution of pH 7.0. The vaccines were ready to use after being stirred well. 40 14-day-old piglets were selected and divided into 8 groups, 5 pigs per group. There were 7 groups as the immunization groups, and the control group was the 8th group, which was not immunized and served as the challenge control group. The specific immunization methods are shown in Table 5.

TABLE 5

Immunization grouping of Mycoplasma pneumonia vaccines

| Group | Type of vaccine | Number of piglets | Age | Dose (ml) |
|---|---|---|---|---|
| Vaccine E | Added 50% (v/v) adjuvant prepared according to Test example 2 of Example 7 | 5 | 14-day-old | 2 ml |
| Vaccine F | Added 50% (v/v) adjuvant prepared according to Test example 3 of Example 7 | 5 | | |
| Vaccine G | Added 50% (v/v) adjuvant prepared according to Test example 6 of Example 7 | 5 | | |
| Vaccine H | Added 50% (v/v) adjuvant prepared according to Test example 7 of Example 7 | 5 | | |
| Contrast vaccine E1 | Added 10% (v/v) GEL01 (Seppic) | 5 | | |
| Contrast vaccine F1 | Added 50% (v/v) 206 adjuvant (Seppic) | 5 | | |
| Contrast vaccine G1 | Added 50% (v/v) adjuvant prepared according to contrast example 5 of Example 7 | 5 | | |
| Chanlleng control group | | 5 | / | / |

After 70 days after immunization, *Mycoplasma hyopneumoniae* was used for the challenge test. The vaccinated and control piglets were intratracheally injected with 5 mL/piglet (100 MID) of CVCC354 strain (purchased from China Institute of Veterinary Drug Control). After 30 days of observation after challenge, the test pigs were sacrificed, and the lung lesions of the test pigs were scored according to the scoring criteria of index of lung lesions of the *Mycoplasma hyopneumoniae*. The immunization group and the control group were analyzed for differences in index of lung lesions.

TABLE 6

Scores of lung injury of pigs in each test group challenged by Mycoplasma hyopneumoniae

| Type of vaccine | Number of piglets | Mean index of lung lesions + standard deviation |
|---|---|---|
| Vaccine E | 5 | 9.92 ± 1.14 |
| Vaccine F | 5 | 9.99 ± 1.31 |
| Vaccine G | 5 | 2.67 ± 1.25 |
| Vaccine H | 5 | 3.83 ± 1.59 |
| Contrast vaccine E1 | 5 | 9.86 ± 1.45 |
| Contrast vaccine F1 | 5 | 4.43 ± 1.56 |
| Contrast vaccine G1 | 5 | 10.37 ± 1.57 |
| Control group | 5 | 16.20 ± 1.51 |

The test results showed that vaccine E, vaccine F, contrast vaccine E1, and contrast vaccine G1 all showed more serious lung disease after one single-shot immunization, and vaccine G group, vaccine H group and contrast vaccine F1 group had low lung lesion scores and better immune effect, but 1 of the 5 pigs in contrast vaccine F1 group had side effects, which were manifested as fever and reduced food intake. This shows that the vaccines prepared by the adjuvant composition of Test examples 6-7 of the present disclosure can protect against the challenge by *Mycoplasma hyopneumoniae* without side effects after immunization.

Example 11. The Adjuvant Composition of the Present Disclosure was Used for Vaccine Dilution Test 1. Preparation of Contrast Adjuvants Contrast example I, an adjuvant was prepared according to the adjuvant 5 of Dong Lu's master thesis *Study of Adjuvants for Inactivated Vaccine and Live Vaccine of Porcine Mycoplasma Pneumonia*, which contained carbomer and ISCOM, and *Mycoplasma hyopneumoniae* HN0613 strain was used as an antigen.

Contrast example II, an adjuvant was prepared according to Example 1 of Chinese Patent CN1305524C, which contained squalane, pluronic L121 and carbomer, and *Mycoplasma hyopneumoniae* HN0613 strain was used as an antigen.

2. Live Vaccine Dilution Test

The vaccines A~H, the contrast vaccines A1, G1 prepared in Example 9 and Example 10 and the contrast vaccines I, and II were used to dilute the porcine reproductive and respiratory syndrome live vaccine (JXA1-R strain), the swine fever live vaccine (attenuated strain of Hog cholera lapinized virus) and pseudorabies live vaccine (Bartha-K61 strain) at the same time, and meanwhile the same volume of sterile water for injection was used to dilute the above live vaccines to obtain reference diluents. Following the instructions for use, the inactivated vaccine part is reconstituted with 1 piglet dosage/bottle (2 ml). After being placed at 20±3° C. for 3 hours, the live virus content of the two diluents were measured according to the virus content determination methods of the respective quality standards of the three live vaccines. The results are shown in Table 7.

TABLE 7

Test results of the live vaccines diluted by the vaccines prepared by the adjuvants of the present disclosure

| Group | Swine fever live vaccine | | Porcine reproductive and respiratory syndrome live vaccine | | Pseudorabies live vaccine | |
|---|---|---|---|---|---|---|
| | Diluted with inactivated vaccine ($TCID_{50}$) | Diluted with reference diluent ($TCID_{50}$) | Diluted with inactivated vaccine ($TCID_{50}$) | Diluted with reference diluent ($TCID_{50}$) | Diluted with inactivated vaccine ($TCID_{50}$) | Diluted with reference diluent ($TCID_{50}$) |
| Vaccine A | $10^{4.5}$ | $10^{4.7}$ | $10^{3.5}$ | $10^{3.6}$ | $10^{5.6}$ | $10^{5.8}$ |
| Vaccine B | $10^{4.6}$ | $10^{4.7}$ | $10^{3.2}$ | $10^{3.6}$ | $10^{5.5}$ | $10^{5.8}$ |
| Vaccine C | $10^{4.5}$ | $10^{4.7}$ | $10^{3.1}$ | $10^{3.6}$ | $10^{5.4}$ | $10^{5.8}$ |
| Vaccine D | $10^{4.6}$ | $10^{4.7}$ | $10^{3.5}$ | $10^{3.6}$ | $10^{5.7}$ | $10^{5.8}$ |
| Vaccine E | $10^{4.6}$ | $10^{4.7}$ | $10^{3.2}$ | $10^{3.6}$ | $10^{5.6}$ | $10^{5.8}$ |
| Vaccine F | $10^{4.5}$ | $10^{4.7}$ | $10^{3.5}$ | $10^{3.6}$ | $10^{5.3}$ | $10^{5.8}$ |
| Vaccine G | $10^{4.6}$ | $10^{4.7}$ | $10^{3.1}$ | $10^{3.6}$ | $10^{5.5}$ | $10^{5.8}$ |
| Vaccine H | $10^{4.6}$ | $10^{4.7}$ | $10^{3.2}$ | $10^{3.6}$ | $10^{5.7}$ | $10^{5.8}$ |
| Contrast vaccine A1 | $10^{4.0}$ | $10^{4.7}$ | $10^{3.5}$ | $10^{3.6}$ | $10^{3.4}$ | $10^{5.8}$ |
| Contrast vaccine G1 | $10^{1.0}$ | $10^{4.7}$ | 0 | $10^{3.6}$ | 0 | $10^{5.8}$ |
| Contrast vaccine I | $10^{1.0}$ | $10^{4.7}$ | 0 | $10^{3.6}$ | 0 | $10^{5.8}$ |
| Contrast vaccine II | $10^{1.0}$ | $10^{4.7}$ | 0 | $10^{3.6}$ | 0 | $10^{5.8}$ |

According to the regulations in the field, the effect of the adjuvant compositions of the present disclosure on the viral activity is evaluated by comparison with the reference diluents, and the differences were all not more than 0.7 log 10 (European Veterinary Vaccine Standard), then the inactivated vaccines or subunit vaccines for diluting live vaccines were judged to be qualified. Therefore, the vaccine of the present disclosure can be used as a diluent for lyophilized live virus antigens. Contrast vaccine I, contrast vaccine II, and contrast vaccine G1 have a significant virus-killing effect and cannot be used as adjuvants for inactivated vaccines or subunit vaccines to dilute the live vaccine. The contrast vaccine A1 can only be used for dilution of part of the live vaccines, not for all three vaccines.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art may make some equivalent variations or modifications to the above-disclosed technical content without departing from the scope of the technical solutions of the present disclosure to obtain equivalent examples. Without departing from the contents of the technical solutions of the present disclosure, any simple modifications, equivalent changes and modifications made to the above examples according to the technical essence of the present disclosure all fall within the scope of the technical solutions of the present disclosure.

The invention claimed is:

1. A composition comprising 0.2%-0.5% w/v carbomer, 0.1%-0.5% w/v Lecithin, and 0.03%-0.2% w/v ginseng stem-leaf saponins.

2. The composition according to claim 1, wherein the composition contains 0.2%-0.5% w/v carbomer, 0.1%-0.4% w/v lecithin and 0.03%-0.2% w/v ginseng stem-leaf saponins.

3. The composition according to claim 1 further comprising 0.05%-0.2% w/v polyinosinic acid-polycytidylic acid or derivatives thereof.

4. The composition according to claim 1, wherein the composition contains 0.2%-0.5% w/v carbomer, 0.1%-0.2% w/v lecithin and 0.03%-0.2% w/v ginseng stem-leaf saponins.

5. The composition according to claim 1, wherein the composition contains 0.4% w/v carbomer, 0.1% w/v lecithin and 0.05% w/v ginseng stem-leaf saponins.

6. A vaccine composition comprising 30-70% w/w of a composition including 0.2%-0.5% w/v carbomer, 0.1%-0.5% w/v Lecithin and 0.03%-0.2% w/v ginseng stem-leaf saponins and an immune amount of inactivated antigen or subunit antigen.

7. The vaccine composition according to claim 6, wherein the inactivated antigen is a porcine circovirus antigen, a *Mycoplasma hyopneumoniae* antigen or a porcine pseudorabies virus antigen.

8. The vaccine composition according to claim 6, wherein the vaccine composition contains 0.2% w/v carbomer, 0.05% w/v lecithin, 0.015%-0.05% w/v ginseng stem-leaf saponins and 100 μg/ml PCV2 protein virus-like particle antigen.

9. The vaccine composition according to claim 6, wherein the vaccine composition contains 0.2% w/v carbomer, 0.05% w/v lecithin, 0.025% w/v ginseng stem-leaf saponins, 0.025%-0.1% w/v polyinosinic acid-polycytidylic acid or derivatives thereof and 100 μg/ml PCV2 protein virus-like particle antigen.

10. The vaccine composition according to claim 6 wherein the composition is 50% w/w.

11. A vaccine composition comprising 30-70% w/w of a composition including 0.2%-0.5% w/v carbomer, 0.1%-0.5% w/v Lecithin and 0.03%-0.2% w/v ginseng stem-leaf saponins, an immune amount of inactivated antigen or subunit antigen and an immune amount of live virus vaccine.

* * * * *